(12) United States Patent
Ishikawa

(10) Patent No.: US 12,732,683 B2
(45) Date of Patent: Sep. 8, 2026

(54) IMAGE PICKUP UNIT, METHOD OF MANUFACTURING IMAGE PICKUP UNIT, AND ENDOSCOPE

(71) Applicant: OLYMPUS MEDICAL SYSTEMS CORP., Tokyo (JP)

(72) Inventor: Shinya Ishikawa, Fuchu (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 701 days.

(21) Appl. No.: 18/198,941

(22) Filed: May 18, 2023

(65) Prior Publication Data

US 2023/0291988 A1 Sep. 14, 2023

Related U.S. Application Data

(63) Continuation of application No. PCT/JP2021/018950, filed on May 19, 2021.

(51) Int. Cl.
*H04N 23/00* (2023.01)
*A61B 1/00* (2006.01)
(Continued)

(52) U.S. Cl.
CPC ......... *H04N 23/555* (2023.01); *A61B 1/0011* (2013.01); *A61B 1/05* (2013.01)

(58) Field of Classification Search
CPC ............ G02B 23/2484; G02B 23/2423; G02B 23/2476; G02B 23/243; G02B 23/2469;
(Continued)

(56) References Cited

U.S. PATENT DOCUMENTS 6,567,115 B1 * 5/2003 Miyashita .............. A61B 1/051 348/76
2014/0003018 A1 1/2014 Fujimori
(Continued)

FOREIGN PATENT DOCUMENTS

CN 112470057 A * 3/2021 ............. H04N 23/54
EP 2 683 225 A1 1/2014
(Continued)

OTHER PUBLICATIONS

International Search Report dated Aug. 17, 2021 received in PCT/JP2021/018950.

*Primary Examiner* — Pete T Lee
(74) *Attorney, Agent, or Firm* — Scully, Scott, Murphy & Presser, P.C.

(57) ABSTRACT

An image pickup unit includes: an image pickup substrate; a first wiring plate bonded to the image pickup substrate; and a second wiring plate having a fifth principal surface, a sixth principal surface, and a second side surface, a fifth electrode on the fifth principal surface and a sixth electrode on the second side surface being bonded to a fourth electrode on the fourth principal surface of the first wiring plate by using solder, the sixth electrode being extended from the fifth electrode. A first conductor block is embedded in the second wiring plate, an exposed surface of the first conductor block on the fifth principal surface being the fifth electrode, an exposed surface of the first conductor block on the second side surface being the sixth electrode. The solder bonding the fourth and sixth electrodes forms a fillet.

16 Claims, 12 Drawing Sheets

(51) Int. Cl.
*A61B 1/05* (2006.01)
*H04N 23/50* (2023.01)

(58) Field of Classification Search
CPC ............ G02B 23/2446; G02B 23/2461; G02B 6/4212; G02B 6/424; G02B 6/4242; G02B 23/24; G02B 7/021; H05K 1/0284; H05K 1/183; H05K 2201/10121; H05K 2203/1305; H05K 2203/1316; H05K 3/10; H05K 3/284
See application file for complete search history.

(56) References Cited

U.S. PATENT DOCUMENTS

| | | | |
|---|---|---|---|
| 2017/0127921 | A1 | 5/2017 | Motohara et al. |
| 2017/0164818 | A1 | 6/2017 | Ishikawa et al. |

FOREIGN PATENT DOCUMENTS

| | | | | |
|---|---|---|---|---|
| EP | 3 231 350 | A1 | | 10/2017 |
| EP | 3 244 603 | A1 | | 11/2017 |
| JP | S59-94441 | A | | 5/1984 |
| JP | 2007-294798 | A | | 11/2007 |
| JP | 2012-186301 | A | | 9/2012 |
| JP | 2016-036558 | A | | 3/2016 |
| JP | 6013657 | B1 | | 10/2016 |
| JP | 6038424 | B1 | | 12/2016 |
| JP | 2017023234 | A | * | 2/2017 |
| JP | 2020-039427 | A | | 3/2020 |
| WO | 2012/120742 | A1 | | 9/2012 |
| WO | 2016/092986 | A1 | | 6/2016 |
| WO | 2016/111075 | A1 | | 7/2016 |

* cited by examiner

1
O
10SA
20SA
50
15
29
30SA
39
10
10SS1
49
70
49A
40SA
45A
45
50SA
60SA
21
59
69
20SS1
20
20SS2
70SA
38(31)
30SS1
30
30SS2
80SA
60
90SA
48(41)
40SS1
40
40SS2
100SA
X
Y
Z

FIG. 14
FIG. 15
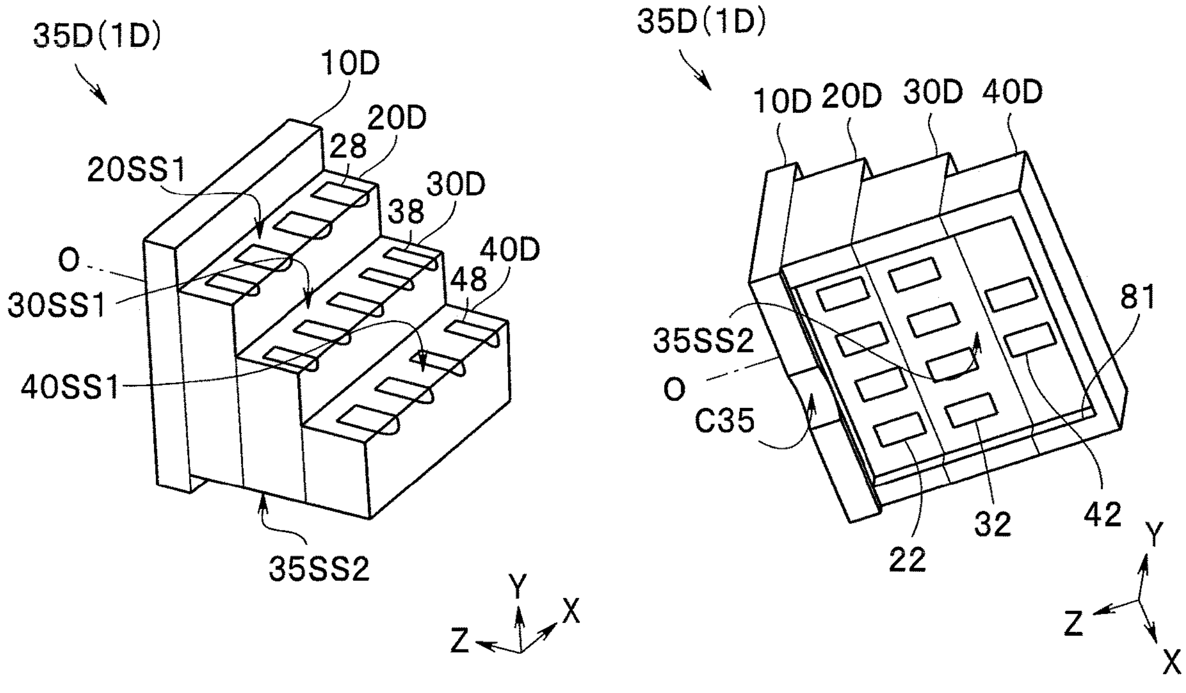
FIG. 16
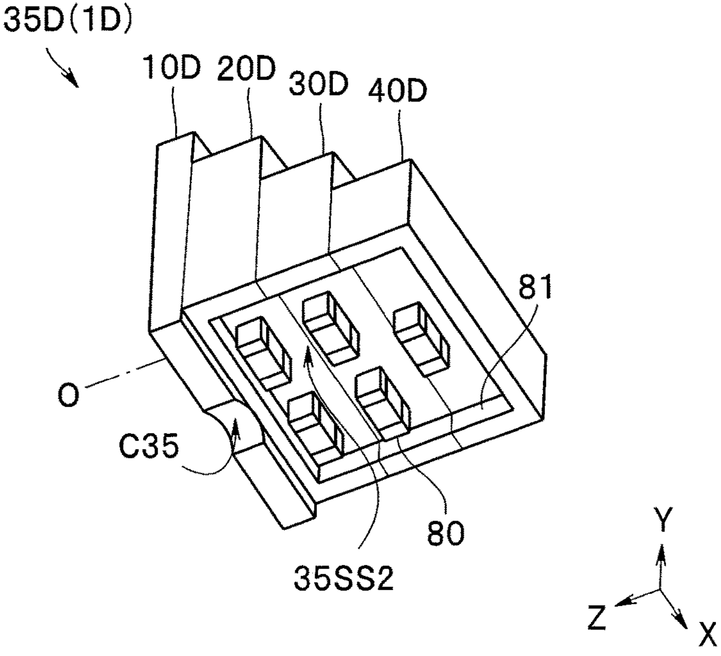

IMAGE PICKUP UNIT, METHOD OF MANUFACTURING IMAGE PICKUP UNIT, AND ENDOSCOPE

CROSS REFERENCE TO RELATED APPLICATION

This application is a continuation application of PCT/JP2021/018950 filed on May 19, 2021, the entire contents of which are incorporated herein by this reference.

BACKGROUND OF THE INVENTION

1. Field of the Invention

The present invention relates to an image pickup unit in which a plurality of wiring plates are bonded, a method of manufacturing the image pickup unit, and an endoscope including the image pickup unit.

2. Description of the Related Art

International Publication No. 2016/092986 discloses an image pickup unit including an image pickup device, a circuit board, an irregularly-shaped substrate in which an electronic component is housed, and a cable. The image pickup device is bonded to the circuit board by using solder balls. A back surface of the circuit board is bonded to a front surface of the irregularly-shaped substrate by soldering or ultrasound.

SUMMARY OF THE INVENTION

An image pickup unit of an embodiment includes: an image pickup substrate having a first principal surface and a second principal surface and including an image pickup device, a first electrode of the image pickup device being connected to a second electrode disposed on the second principal surface; a first wiring plate having a third principal surface, a fourth principal surface, and a first side surface, a third electrode on the third principal surface being bonded to the second electrode; and a second wiring plate having a fifth principal surface, a sixth principal surface, and a second side surface, a fifth electrode on the fifth principal surface and a sixth electrode on the second side surface being bonded to a fourth electrode on the fourth principal surface of the first wiring plate by using solder, the sixth electrode being extended from the fifth electrode. A first conductor block is embedded in the second wiring plate, an exposed surface of the first conductor block on the fifth principal surface being the fifth electrode, an exposed surface of the first conductor block on the second side surface being the sixth electrode. The solder bonding the fourth and sixth electrodes forms a fillet.

An image pickup unit of an embodiment includes: an image pickup substrate having a first principal surface and a second principal surface and including an image pickup device, a first electrode of the image pickup device being connected to a second electrode disposed on the second principal surface; a first wiring plate having a third principal surface, a fourth principal surface, and a first side surface, a third electrode on the third principal surface being bonded to the second electrode; a second wiring plate having a fifth principal surface, a sixth principal surface, and a second side surface, the second wiring plate being a multi-layer board in which a plurality of wiring layers are stacked in an optical axis direction, an interval between two wiring layers in each of which a third conductor block and a fourth conductor block are embedded among the plurality of wiring layers being substantially equal to an interval between two chip electrodes of a chip component: the chip component the two chip electrodes of which are bonded to two chip lands that are exposed surfaces of the fourth conductor blocks of the two wiring layers, the exposed surfaces being exposed on the second side surface; and a cable bonded to any of cable lands that are exposed surfaces of the third conductor blocks of the two wiring layers, the exposed surfaces being exposed on a side surface opposite the second side surface. A disposition pitch between the chip lands is equal to a disposition pitch between the cable lands in the optical axis direction.

An endoscope of an embodiment includes an image pickup unit, the image pickup unit includes: an image pickup substrate having a first principal surface and a second principal surface and including an image pickup device, a first electrode of the image pickup device being connected to a second electrode disposed on the second principal surface; a first wiring plate having a third principal surface, a fourth principal surface, and a first side surface, a third electrode on the third principal surface being bonded to the second electrode; and a second wiring plate having a fifth principal surface, a sixth principal surface, and a second side surface, a fifth electrode on the fifth principal surface and a sixth electrode on the second side surface being bonded to a fourth electrode on the fourth principal surface of the first wiring plate by using solder, the sixth electrode being extended from the fifth electrode. A first conductor block is embedded in the second wiring plate, an exposed surface of the first conductor block on the fifth principal surface being the fifth electrode, an exposed surface of the first conductor block on the second side surface being the sixth electrode. The solder bonding the fourth and sixth electrodes forms a fillet.

A method of manufacturing an image pickup unit of an embodiment includes: producing an image pickup substrate having a first principal surface and a second principal surface and including an image pickup device, a first electrode of the image pickup device being connected to a second electrode disposed on the second principal surface; producing a first wiring plate having a third principal surface and a fourth principal surface, including a third electrode on the third principal surface, and including a fourth electrode on the fourth principal surface; producing a stack sheet in which a first wiring sheet including a hole filled with a conductor block and a second wiring sheet are stacked; cutting the stack sheet along a cut line across the hole to produce a second substrate having a fifth principal surface, a sixth principal surface, and a second side surface, including a fifth electrode that is an exposed surface of the conductor block on the fifth principal surface, and including a sixth electrode that is a cut surface of the conductor block on the second side surface; producing a third substrate having a seventh principal surface and a third side surface and including a cable land on the third side surface; integrating the second and third substrates by stacking with the sixth principal surface of the second substrate being in contact with the seventh principal surface of the third substrate, and then firing the second and third substrates to produce a solid wiring plate including a second wiring plate and a third wiring plate; bonding the second electrode of the image pickup substrate to the third electrode of the first wiring plate; bonding the fourth electrode of the first wiring plate to the fifth and sixth electrodes of the second wiring plate by using solder; and bonding a cable to the cable land of the third wiring plate.

BRIEF DESCRIPTION OF THE DRAWINGS

FIG. 14 is a perspective view of wiring plates of an image pickup unit according to Modification 2 of the second embodiment;

FIG. 15 is a perspective view of the wiring plates of the image pickup unit according to Modification 2 of the second embodiment;

FIG. 16 is a perspective view of the wiring plates of the image pickup unit according to Modification 2 of the second embodiment;

DETAILED DESCRIPTION OF THE PREFERRED EMBODIMENTS

First Embodiment

Figure 1:
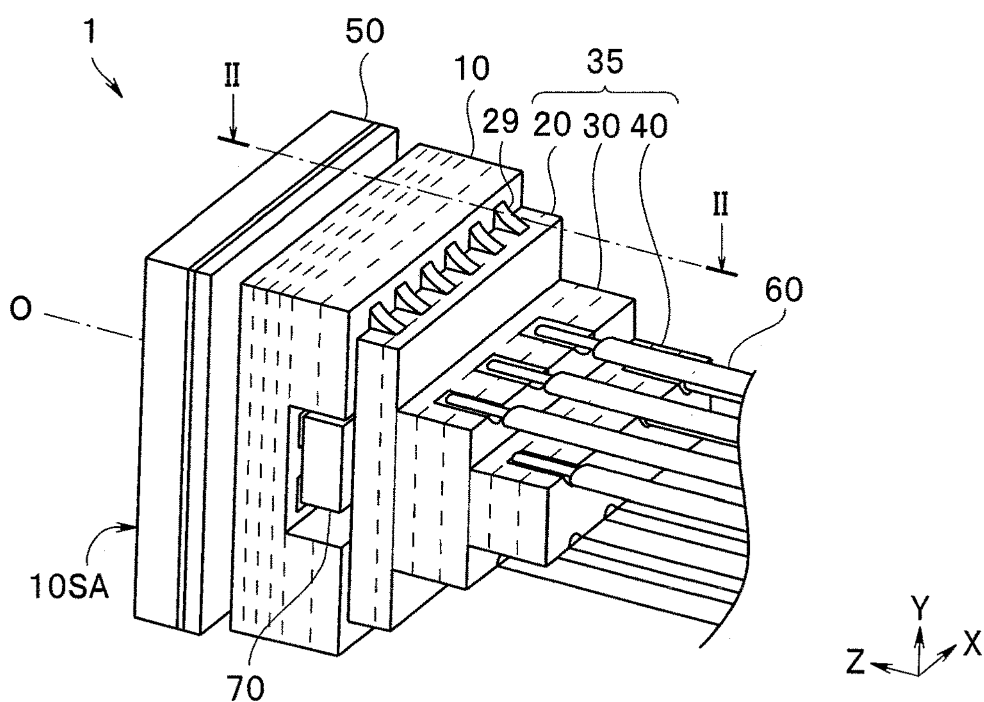
FIG. 1 is a perspective view of an image pickup unit according to a first embodiment.
Figure 2:
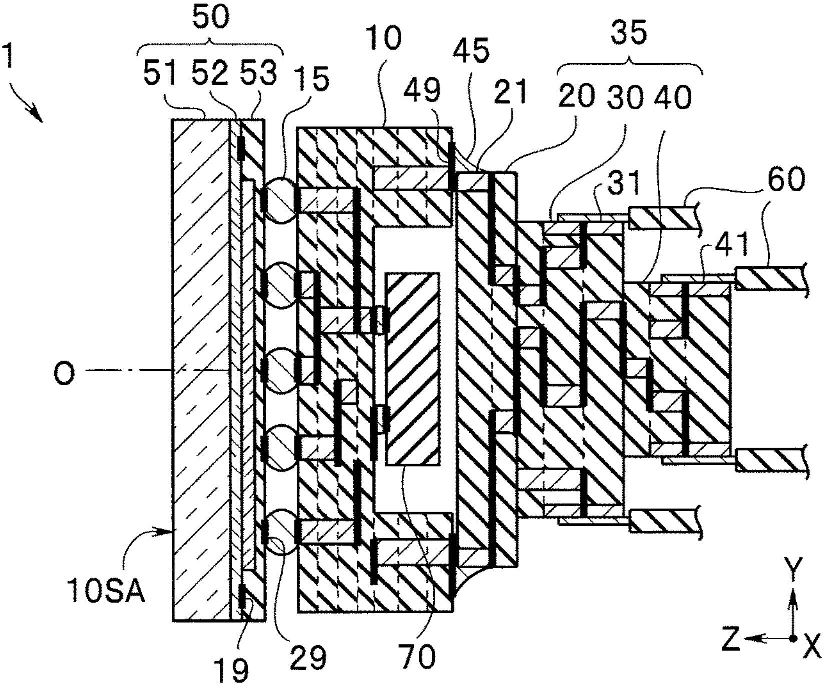
FIG. 2 is a cross-sectional view taken along line II-II in FIG. 1.
Figure 3:
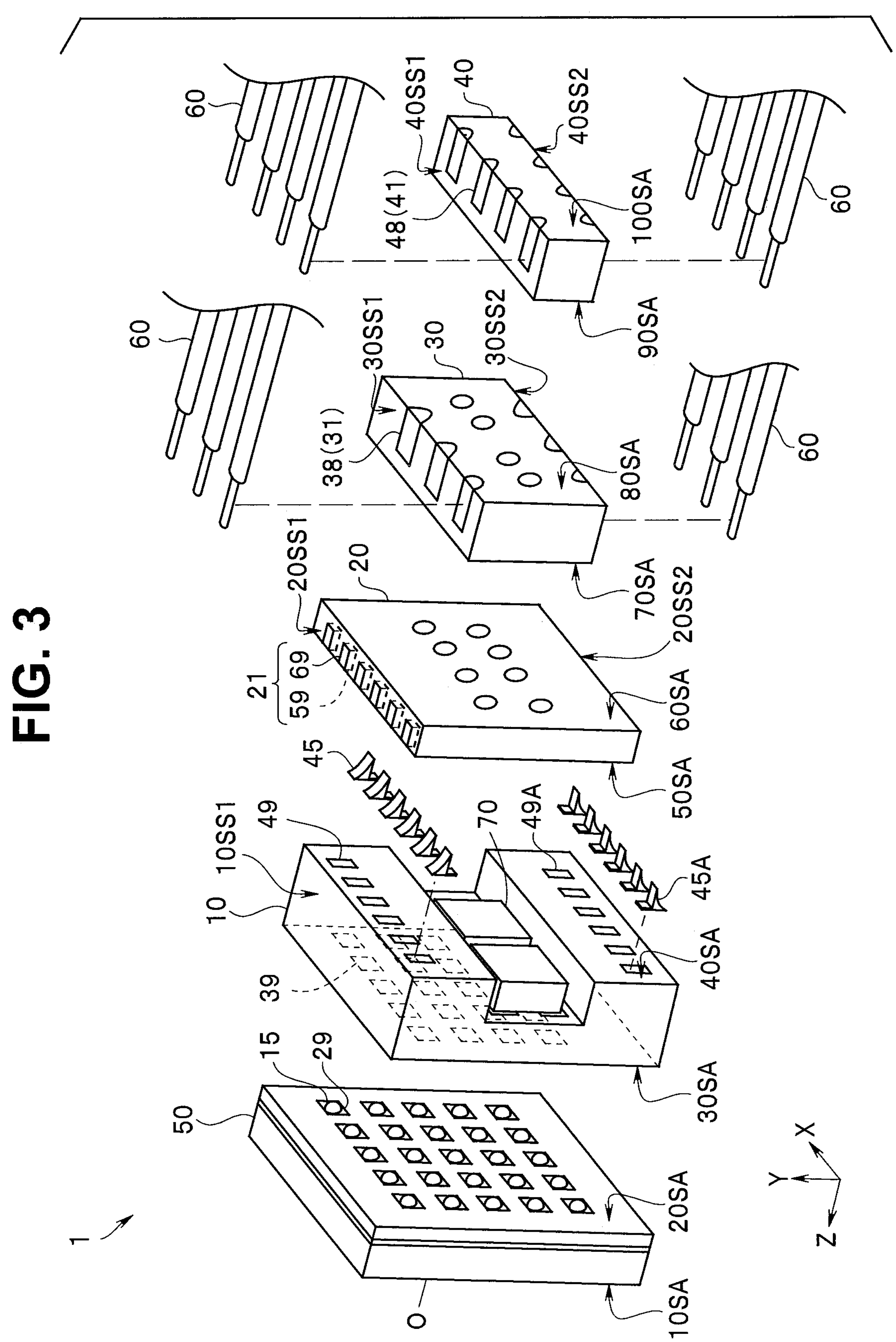
FIG. 3 is a perspective exploded view of the image pickup unit according to the first embodiment.

FIGS. 1, 2, 3 and 4 illustrate an image pickup unit 1 according to the present embodiment. The image pickup unit 1 includes an image pickup substrate 50, a first wiring plate 10, a solid wiring plate 35, and a cable 60. The solid wiring plate 35 includes a second wiring plate 20, a third wiring plate 30, and a fourth wiring plate 40. Although the solid wiring plate (solid wiring unit) 35 includes the three bonded wiring plates, the solid wiring plate may be manufactured by integral molding or the like.

Note that, in description below, diagrams based on embodiments are schematic. A relation between thickness and width of each part, a thickness ratio of each part, and the like are different from those in reality. A dimensional relation and a ratio are different between parts of drawings in some cases. Illustration and reference sign provision of some constituent components are omitted.

The image pickup substrate 50 has a first principal surface 10SA that is a light-receiving surface, and a second principal surface 20SA opposite the first principal surface 10SA. The image pickup substrate 50 includes a cover glass 51, an image pickup device 53, and a bonding layer 52 bonding the cover glass 51 and the image pickup device 53. A plurality of second electrodes 29 are disposed on the second principal surface 20SA that is a back surface of the image pickup device 53 on which image pickup light is received. A light receiving circuit and a plurality of first electrodes 19 are disposed on a light-receiving surface of the image pickup device 53. The first electrodes 19 are connected to the second electrodes 29 via through wires.

Note that one or more semiconductor elements configured to process an image pickup signal are stacked on the back surface of the image pickup device 53, and the second electrodes 29 may be disposed on back surfaces of the semiconductor elements, which are the second principal surface 20SA of the image pickup substrate 50.

The first wiring plate (first wiring unit) 10 has a third principal surface 30SA, a fourth principal surface 40SA opposite the third principal surface 30SA, and a first side surface 10SS1 orthogonal to the third principal surface 30SA and the fourth principal surface 40SA. A plurality of third electrodes 39 are disposed on the third principal surface 30SA. The third electrodes 39 are bonded to the second electrodes 29 by using solder 15. A plurality of fourth electrodes 49 are disposed on the fourth principal surface 40SA. A recess (cavity) in which an electronic component 70 is housed is formed on the fourth principal surface 40SA.

The first wiring plate 10 is a ceramic wiring plate (ceramic wiring unit) including a plurality of ceramic wiring layers. The electronic component 70 is bonded to an electrode (not illustrated) on a bottom surface of the cavity. The electronic component 70 is, for example, a capacitor or IC connected to the image pickup device 53.

The second electrodes 29 on the second principal surface 20SA of the image pickup substrate 50 are bonded to the third electrodes 39 on the third principal surface 30SA of the first wiring plate 10 by the solder 15.

Note that a space between the second principal surface 20SA and the third principal surface 30SA, and inside of the cavity may be filled with sealing resin.

The solid wiring plate 35 is a ceramic wiring plate (solid ceramic wiring unit) in which the second wiring plate 20, the third wiring plate 30, and the fourth wiring plate 40 each including a plurality of ceramic wiring layers are stacked and integrated.

The second wiring plate 20 (second wiring unit) has a fifth principal surface 50SA, a sixth principal surface 60SA opposite the fifth principal surface 50SA, and a second side surface 20SS1 orthogonal to the fifth principal surface 50SA and the sixth principal surface 60SA. A plurality of fifth electrodes 59 are disposed on the fifth principal surface 50SA. A plurality of sixth electrodes 69 are disposed on the second side surface 20SS1.

Figure 4:
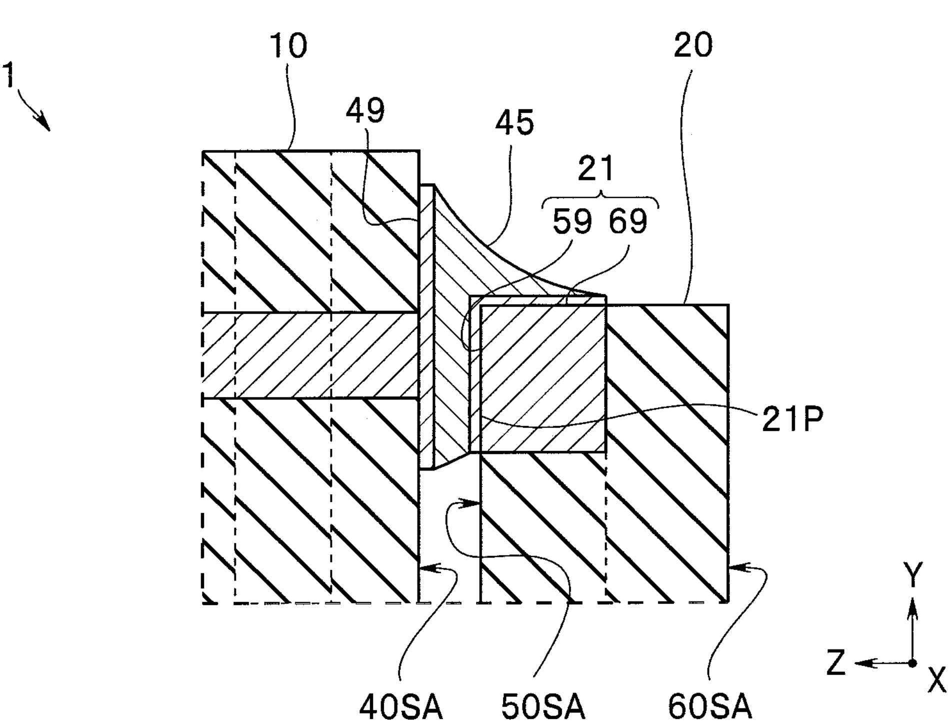
FIG. 4 is a partial cross-sectional view of the image pickup unit according to the first embodiment.
Figure 5:
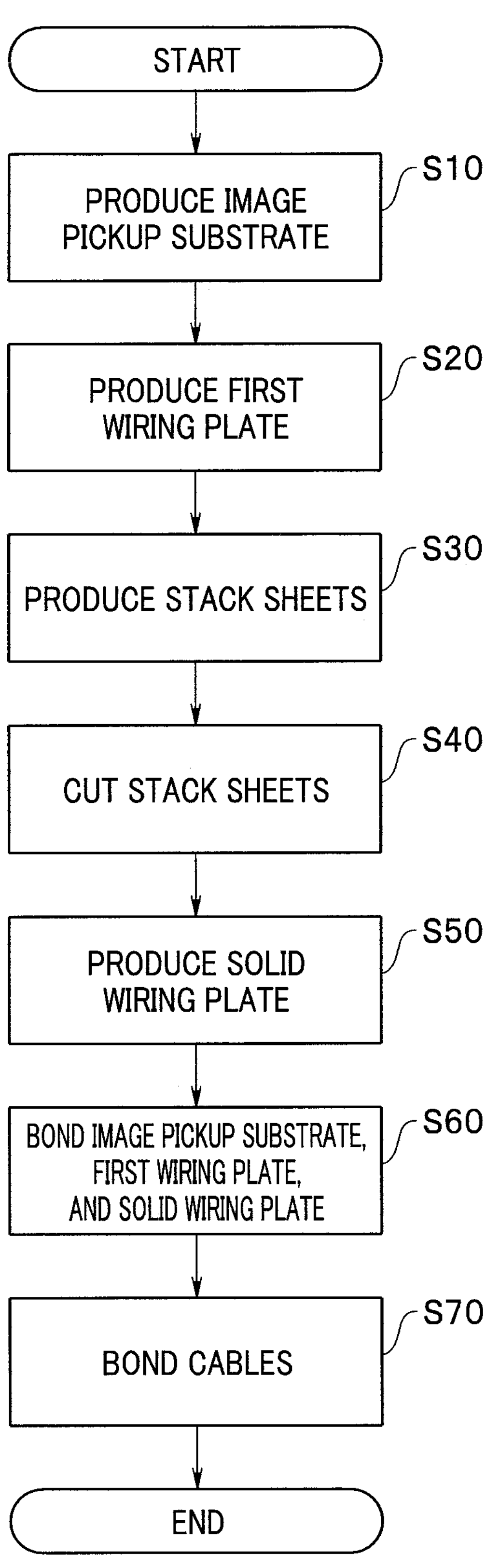
FIG. 5 is a flowchart of a method of manufacturing the image pickup unit according to the first embodiment.

As illustrated in FIG. 4, each fifth electrode 59 and the corresponding sixth electrode 69 are exposed surfaces of a first conductor block 21 embedded in the second wiring plate 20. A conductor block is typically a conductor filling a bottomed hole called via. Note that, as illustrated, for example, a conductive film 21P that is a two-layer plated film made of a nickel layer and a gold layer is additionally disposed on the exposed surfaces of the first conductor block 21 as the fifth electrode 59 and the sixth electrode 69. Thus, an "exposed surface" in the present specification includes an "exposed surface on which a conductive film is disposed".

The third wiring plate 30 (third wiring unit) has a seventh principal surface 70SA, an eighth principal surface 80SA opposite the seventh principal surface 70SA, and a third side surface 30SS1 orthogonal to the seventh principal surface 70SA and the eighth principal surface 80SA. A plurality of cable lands 38 are disposed on the third side surface 30SS1. Each cable land 38 is an exposed surface of a second conductor block 31 on the third side surface 30SS1, the second conductor block 31 being embedded in the third wiring plate 30. The second conductor block 31 is exposed on the eighth principal surface 80SA as well. As described later, a land is an electrode to which the cable 60 is bonded by using solder. For example, a two-layer plated film made of a nickel layer and a gold layer may be disposed in each cable land.

The fourth wiring plate (fourth wiring unit) 40 has a ninth principal surface 90SA, a tenth principal surface 100SA opposite the ninth principal surface 90SA, and a fourth side surface 40SS1 orthogonal to the ninth principal surface 90SA and the tenth principal surface 100SA, Note that the ninth principal surface 90SA and the fourth side surface 40SS1 of the fourth wiring plate 40 have substantially equal sizes. Specifically, a principal surface is a surface orthogonal to an optical axis O of the image pickup substrate 50, and a side surface is a surface parallel to the optical axis O.

A plurality of cable lands 48 are disposed on the fourth side surface 40SS1. Each cable land 48 is an exposed surface of a third conductor block 41 on the fourth side surface 40SS1, the third conductor block 41 being embedded in the fourth wiring plate 40. The third conductor block 41 is exposed on the tenth principal surface 100SA as well.

Note that each cable land 38 may be a conductive film disposed on the third side surface 30SS1 instead of an exposed surface of the second conductor block 31.

However, the cable 60 bonded to each cable land 38 by using solder, which is an exposed surface of the second conductor block 31 on the third side surface 30SS1, has high strength of bonding to the third wiring plate 30 because the solder spreads on an exposed surface of the second conductor block 31 on the eighth principal surface 80SA.

Comparison of projection images projected onto a virtual surface orthogonal to the optical axis O shows that a first projection image of the first wiring plate 10 is smaller than a projection image of the image pickup substrate 50 and contained within the projection image of the image pickup substrate 50. A second projection image of the second wiring plate 20 is smaller than the first projection image and contained within the first projection image. A third projection image of the third wiring plate 30 is smaller than the second projection image and contained within the second projection image. A fourth projection image of the fourth wiring plate 40 is smaller than the third projection image and contained within the third projection image.

The sixth electrodes 69 of the second wiring plate 20, the cable lands 38 of the third wiring plate 30, and the cable lands 48 of the fourth wiring plate 40 are contained within the first projection image of the first wiring plate 10.

The second wiring plate 20, the third wiring plate 30, and the fourth wiring plate 40 are stacked and connected to each other through an internal wire (not illustrated).

Note that the configuration of the solid wiring plate according to the embodiment may be modified as appropriate in accordance with specifications of the image pickup unit. The solid wiring plate 35 only needs to include at least the second wiring plate 20 and the third wiring plate 30. In other words, the fourth wiring plate 40 is not an essential constituent component of the solid wiring plate. Instead, the solid wiring plate may include a fifth wiring plate stacked on the tenth principal surface 100SA of the fourth wiring plate 40.

The cable 60 including a conductive wire is bonded to each of the cable lands 38 and 48. The image pickup substrate 50 receives a drive signal and transmits an image pickup signal through the cables 60.

The fourth electrodes 49 on the fourth principal surface 40SA of the first wiring plate 10 are bonded to the sixth electrodes 69 on the second side surface 20SS1 orthogonal to the fourth principal surface 40SA of the second wiring plate 20 by solder 45. The solder 45 forms a fillet between each fourth electrode 49 and the corresponding sixth electrode 69. The solder 45 also bonds the fourth principal surface 40SA of the second wiring plate 20 and the fifth electrodes 59 on the fifth principal surface 50SA that is parallel thereto.

In the image pickup unit 1, the fourth principal surface 40SA of the first wiring plate 10 is bonded not only to the fifth principal surface 50SA of the second wiring plate 20 but also to the second side surface 20SS1 of the second wiring plate 20. Thus, in the image pickup unit 1, strength of bonding between the first wiring plate 10 and the second wiring plate 20 is higher than in a conventional image pickup unit, which leads to higher reliability. At melting of the solder 45, voids (air bubbles) due to flux vaporization and air inclusion are generated at a bonding surface between wiring plates in some cases. In the image pickup unit 1, the voids in the solder 45 are released from the bonding surface into air and eliminated as the melted solder flows from the bonding surface to an end part side. Accordingly, strength of bonding by the solder 45 is not lowered in the image pickup unit 1.

Note that the image pickup unit 1 is rotationally symmetric by 180° with respect to the optical axis O at a center. For example, the first wiring plate 10 includes electrodes 49A at positions rotationally symmetric by 180° to the fourth electrodes 49. The second side surface 20SS1, the third side surface 30SS1, and the fourth side surface 40SS1 have a side surface 20SS2, a side surface 30SS2, and a side surface 40SS2, respectively, at positions rotationally symmetric by 180°. Non-illustrated solder 45A bonding electrodes on the fifth principal surface to electrodes on the side surface 20SS2 is disposed at a position rotationally symmetric by 180° to the solder 45.

<Method of Manufacturing Image Pickup Unit>

A method of manufacturing the image pickup unit 1 will be described below with reference to a flowchart in FIG. 4.

<Step S10> Image Pickup Substrate Production

In a semiconductor wafer, a light receiving unit such as a CMOS light receiving element is formed on a light-receiving surface by a well-known semiconductor manufacturing method. Then, through wires (not illustrated) are disposed to produce an image pickup device wafer not illustrated) in which the second electrodes 29 connected to the first electrodes on the light-receiving surface are provided on the second principal surface 20SA opposite the light-receiving surface. A glass wafer is bonded to a light-receiving surface of the image pickup device wafer by the bonding layer 52. The image pickup device wafer to which the glass wafer is bonded is cut to produce the image pickup substrate 50 having the first principal surface 10SA and the second principal surface 20SA and including the second electrodes 29 on the second principal surface 20SA.

<Step S20> First Wiring Plate Production

Figure 6:
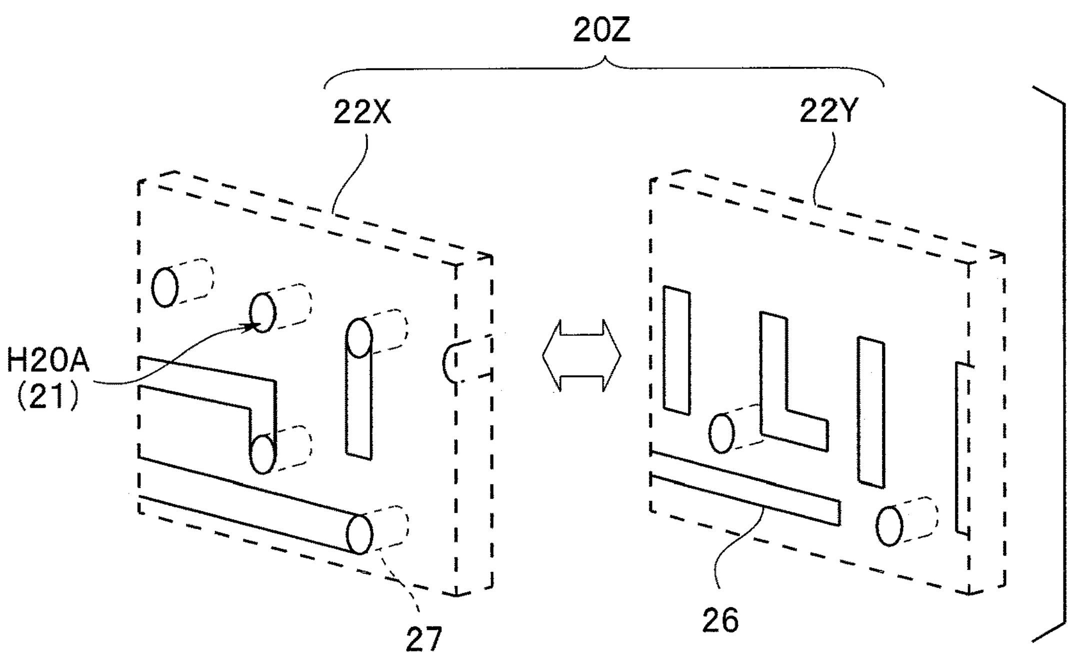
FIG. 6 is a diagram for description of the method of manufacturing the image pickup unit according to the first embodiment.

As illustrated in FIG. 6, the first wiring plate 10 is produced by cutting a first substrate formed by stacking and firing a plurality of wiring sheets. Each wiring sheet is typically a member yet to be fired, which is called green sheet, and includes a predetermined surface wire 26 and a predetermined through wire 27.

The first wiring plate 10 has the third principal surface 30SA and the fourth principal surface 40SA, includes the third electrodes 39 on the third principal surface 30SA, and includes the fourth electrodes 49 on the fourth principal surface 40SA.

The electronic component 70 is mounted on the recess on the fourth principal surface 40SA of the first wiring plate 10.

<Step S30> Stack Sheet Production

As illustrated in FIG. 6, a stack sheet 20Z is produced by stacking a first wiring sheet 22X and a second wiring sheet 22Y, the first wiring sheet 22X having a plurality of holes H20A filled with conductive paste or the like to be the first conductor blocks 21.

Although not illustrated, a stack sheet is produced by stacking a plurality of third wiring sheets including a wiring sheet having holes filled with the second conductor blocks 31. In addition, a stack sheet is produced by stacking a plurality of fourth wiring sheets including a wiring sheet having holes filled with the third conductor blocks 41.

<Step S40> Stack Sheet Cutting

Figure 7:
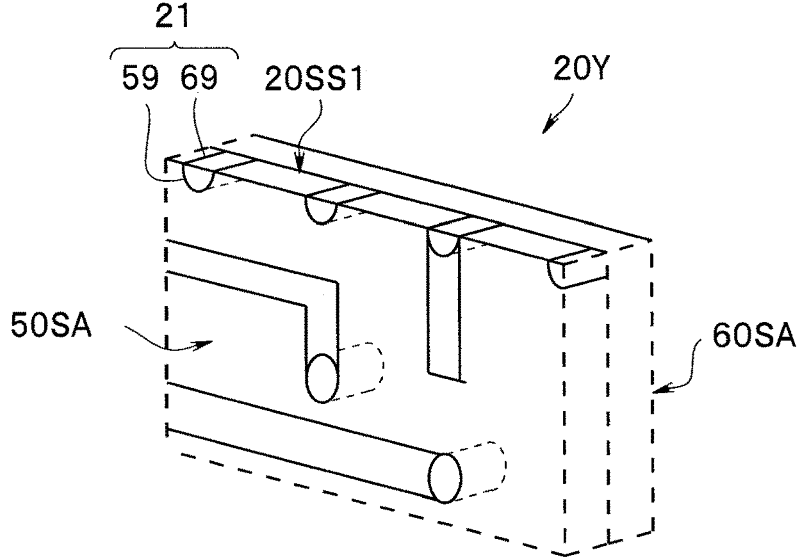
FIG. 7 is a diagram for description of the method of manufacturing the image pickup unit according to the first embodiment.

As illustrated in FIG. 7, the stack sheet 20Z is cut along a cut line across the plurality of holes H20A to produce a second substrate 20Y including the fifth electrodes 59 that are exposed surfaces of the first conductor blocks 21 on the fifth principal surface 50SA and also including the sixth electrodes 69 that are exposed surfaces of the first conductor blocks 21 on the second side surface 20SS1 that is a cut surface. Specifically, each conductor block filling one via of one sheet is cut into conductor blocks (halved via conductors) of two respective sheets.

Although not illustrated, the stack sheet in which the plurality of third wiring sheets are stacked is cut along a cut line across a plurality of holes to produce a third substrate including the cable lands 38 that are cut surfaces (exposed surfaces) of the second conductor blocks 31 on the third side surface 30SS1. The stack sheet in which the plurality of fourth wiring sheets including the wiring sheet having holes filled with the third conductor blocks 41 are stacked is cut along a cut line across holes to produce a fourth substrate including the cable lands 48 that are cut surfaces (exposed surfaces) of the third conductor blocks 41 on the fourth side surface 40SS1.

<Step S50> Solid Wiring Plate Production

The second substrate 20Y, the third substrate, and the fourth substrate are positioned, stacked, and clamped. Then, the second wiring plate 20, the third wiring plate 30, and the fourth wiring plate 40 are fired at a predetermined temperature and integrated into the solid wiring plate 35. Each conductor block made of conductive paste becomes a metal conductor block through the firing. In addition, conductive films may be disposed on electrodes and lands by using a plating method or the like.

<Step S60> Bonding Between Image Pickup Substrate, First Wiring Plate, and Solid Wiring Plate The second electrodes 29 of the image pickup substrate 50 are bonded to the third electrodes 39 of the first wiring plate 10 by using the solder 15. In addition, the fourth electrodes 49 of the first wiring plate 10 are bonded to the fifth electrodes 59 and the sixth electrodes 69 of the solid wiring plate 35 by using the solder 45.

The solder 45 forms a fillet between each fourth electrode 49 and the corresponding sixth electrode 69. In addition, the solder 45 bonds the fourth principal surface 40SA of the second wiring plate 20 to the fifth electrodes 59 on the fifth principal surface 50SA that is parallel thereto.

Needless to say, execution orders of step S10 (image pickup substrate production), step S20 (first wiring plate production), and steps S30 to S50 (solid wiring plate production) may be changed as appropriate, and for example, may be simultaneous.

<Step S70> Cable Bonding

The cables 60 are bonded to the cable lands 38 of the third wiring plate 30 and the cable lands 48 of the fourth wiring plate 40, respectively.

With the method of manufacturing an image pickup unit according to the present embodiment, it is possible to easily manufacture an image pickup unit having high strength of bonding between the first wiring plate 10 and the second wiring plate 20 and having high reliability.

Embodiments and modifications described below are similar to the image pickup unit 1 according to the first embodiment and have the same effects as the image pickup unit 1, and thus any constituent component having the same function is denoted by the same reference sign and description thereof is omitted.

Modification of First Embodiment

Figure 8:
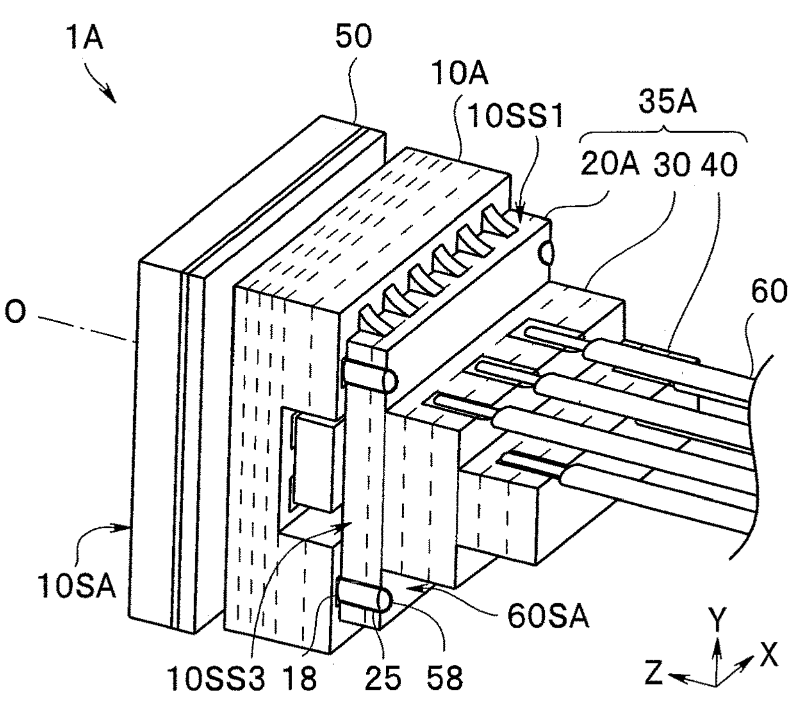
FIG. 8 is a perspective view of an image pickup unit according to a modification of the first embodiment.

In an image pickup unit 1A according to the present modification illustrated in FIG. 8, a second wiring plate 20A includes a groove in a fifth side surface 20SS3 orthogonal to the first side surface 10SS1, the groove having a conductor film 58 as a wall surface. A first wiring plate 10A includes an eighth electrode 18 on the fourth principal surface 40SA. The groove of the second wiring plate 20A is formed by cutting a wiring sheet having a through-hole along a cut line across the through-hole. The conductor film 58 is a nickel plated film or a gold plated film.

Solder 25 filling the groove of the second wiring plate 20A bonds the conductor film 58 and the eighth electrode 18. The image pickup unit 1A is rotationally symmetric by 180° with respect to the optical axis O at the center.

Although the two surfaces of the first wiring plate 10A and the second wiring plate 20A are bonded in the image pickup unit 1, four surfaces including side surfaces are bonded in the image pickup unit 1A. Thus, strength of bonding between the first wiring plate 10A and the second wiring plate 20A in the image pickup unit 1A is higher than in the image pickup unit 1. Moreover, the image pickup unit 1A can transmit an electric signal by using the conductor film 58 and the eighth electrode 18.

Second Embodiment

Figure 9:
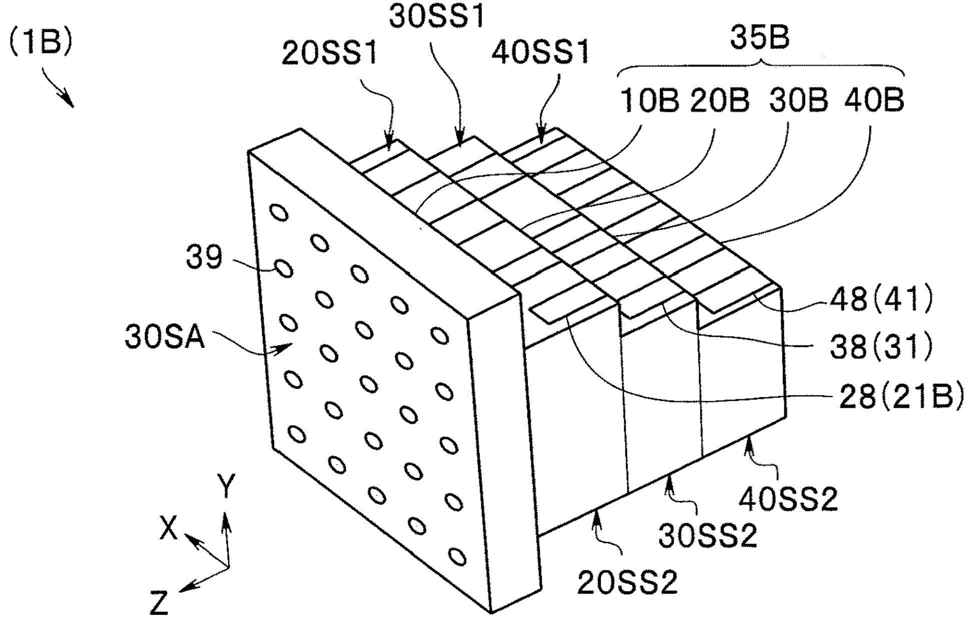
FIG. 9 is a perspective view of wiring plates of an image pickup unit according to a second embodiment.
Figure 10:
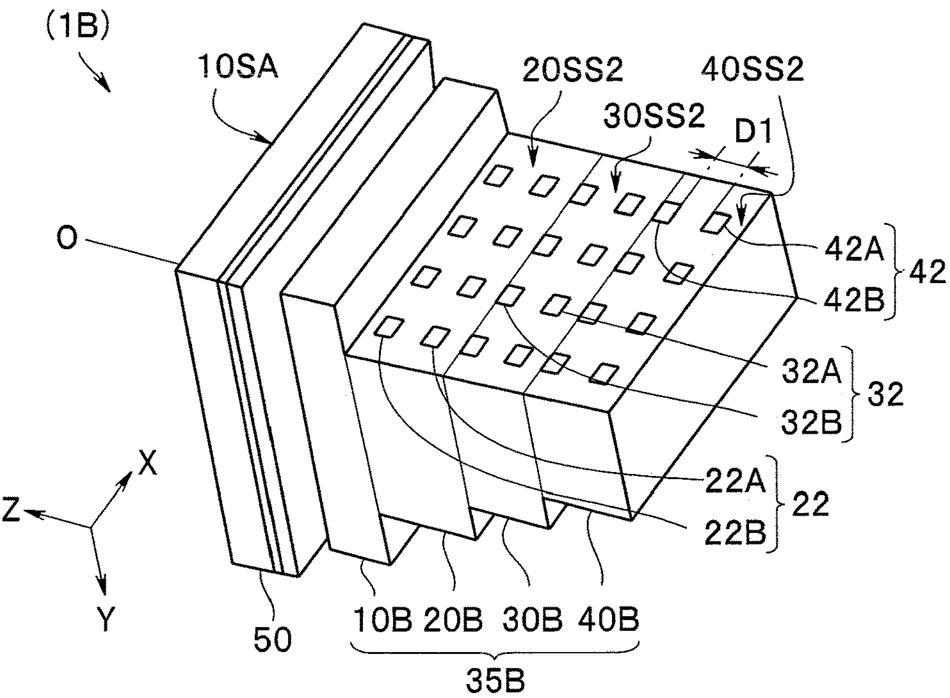
FIG. 10 is a perspective view of the wiring plates of the image pickup unit according to the second embodiment.
Figure 11:
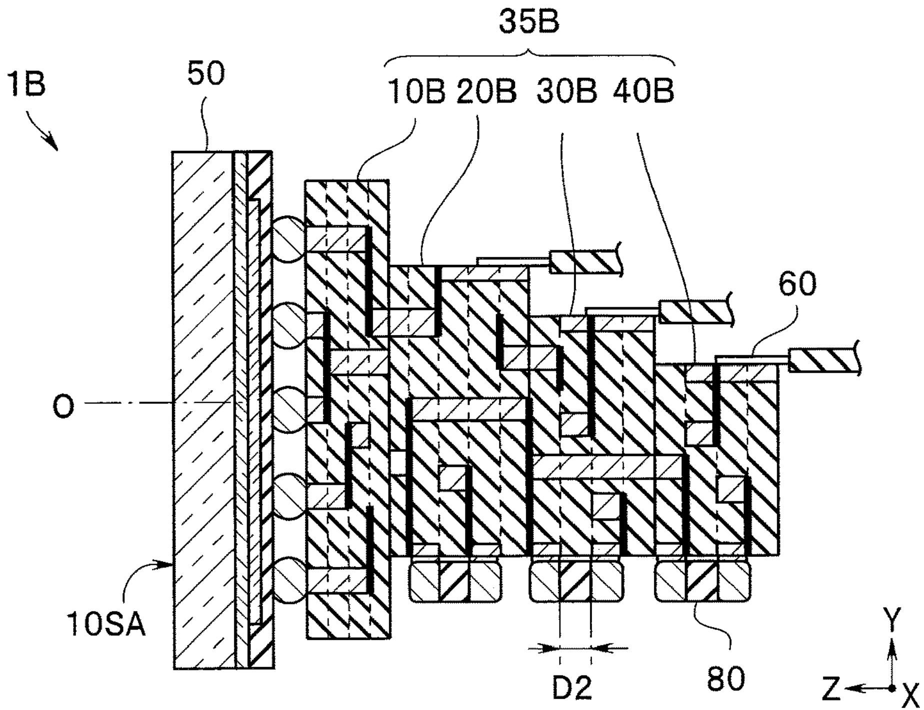
FIG. 11 is a cross-sectional view of the image pickup unit according to the second embodiment.

In an image pickup unit 1B illustrated in FIGS. 9, 10, and 11, a solid wiring plate 35B includes a first wiring plate 10B, a second wiring plate 20B, a third wiring plate 30B, and a fourth wiring plate 40B. The second wiring plate 20B includes cable lands 28 that are exposed surfaces of first conductor blocks 21B on the second side surface 20SS1. The third wiring plate 30B includes the cable lands 38 that are exposed surfaces of the second conductor blocks 31 on the third side surface 30SS1. The fourth wiring plate 40B includes the cable lands 48 that are exposed surfaces of the third conductor blocks 41 on the fourth side surface 40SS1. The cables 60 are bonded to the cable lands 28, 38, and 48.

The side surface 20SS2 parallel to the second side surface 20SS1 of the second wiring plate 20B, the side surface 30SS2 parallel to the third side surface 30SS1 of the third wiring plate 30B, and the side surface 40SS2 parallel to the fourth side surface 40SS1 of the fourth wiring plate 40B form substantially flush planes. Accordingly, the image pickup unit 1B is not rotationally symmetric by 180° with respect to the optical axis O at the center.

The second wiring plate 20B includes two chip lands 22 that are exposed surfaces of two respective fourth conductor blocks 22A and 22B on the side surface 20SS2. The third wiring plate 30B includes two chip lands 32 that are exposed surfaces of two respective fifth conductor blocks 32A and 32B on the side surface 30SS2. The fourth wiring plate 40B includes two chip lands 42 that are exposed surfaces of two respective sixth conductor blocks 42A and 42B on the side surface 40SS2. As described later, a chip electrode of a chip component is mounted on a surface of each chip land by using solder.

As described above, each wiring plate is a multi-layer ceramic substrate in which a plurality of wiring layers are stacked in an optical axis direction, and for example, an interval D1 between the two chip lands 22, 32, or 42 is an interval between two wiring layers.

For example, two chip electrodes of a two-terminal chip component 80 that is a chip capacitor are bonded to the chip lands 22, 32, or 42. Specifically, an interval D2 between the two chip electrodes of each chip component 80 is substantially equal to the interval D1 between the two chip lands 22, 32, or 42.

Note that the configuration in which the interval D1 between wiring layers are substantially equal to the interval D2 between the two chip electrodes of each chip component 80 allows the chip electrodes to be bonded to the chip lands 22, 32, or 42 by soldering.

For example, the plurality of cable lands 28 are disposed on the second side surface 20SS1 of the second wiring plate 20B opposite the side surface 20SS2 at which the plurality of chip lands 22 are disposed. In the second wiring plate 20B that is a stacked ceramic wiring plate, the plurality of chip lands 22 and the plurality of cable lands 28 have the same disposition interval (disposition pitch) in the optical axis direction.

In the image pickup unit 1B, the chip components 80 are mounted near the image pickup device 53. Moreover, in the image pickup unit 1B, a larger number of cables 60 are bonded than in the image pickup unit 1.

In the image pickup unit 1B, since surfaces (20SS2 to 40SS2) on which chip components are mounted and surfaces (20SS1 to 40SS1) to which the cables 60 are bonded are collectively positioned on surfaces opposite each other with respect to the optical axis O, the wiring plates do not need to be turned over when the cables 60 are bonded to the wiring plates by soldering. Moreover, the plurality of wiring plates in the image pickup unit 1B are integrated and thus do not need to be bonded by soldering. For these reasons, the image pickup unit 1B is easy to manufacture.

Modification 1 of Second Embodiment

Figure 12:
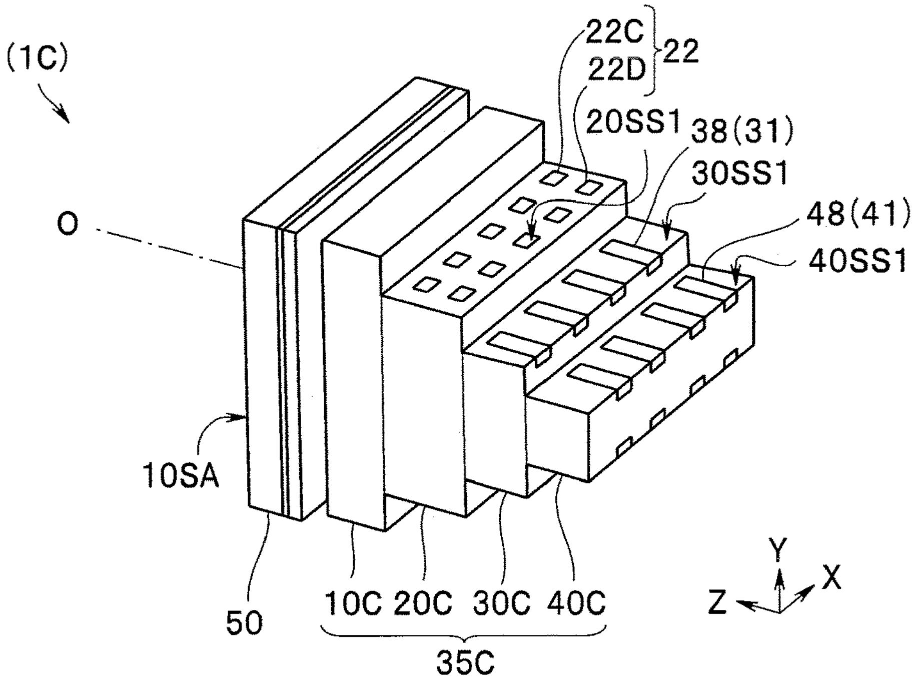
FIG. 12 is a perspective view of an image pickup unit according to Modification 1 of the second embodiment.
Figure 13:
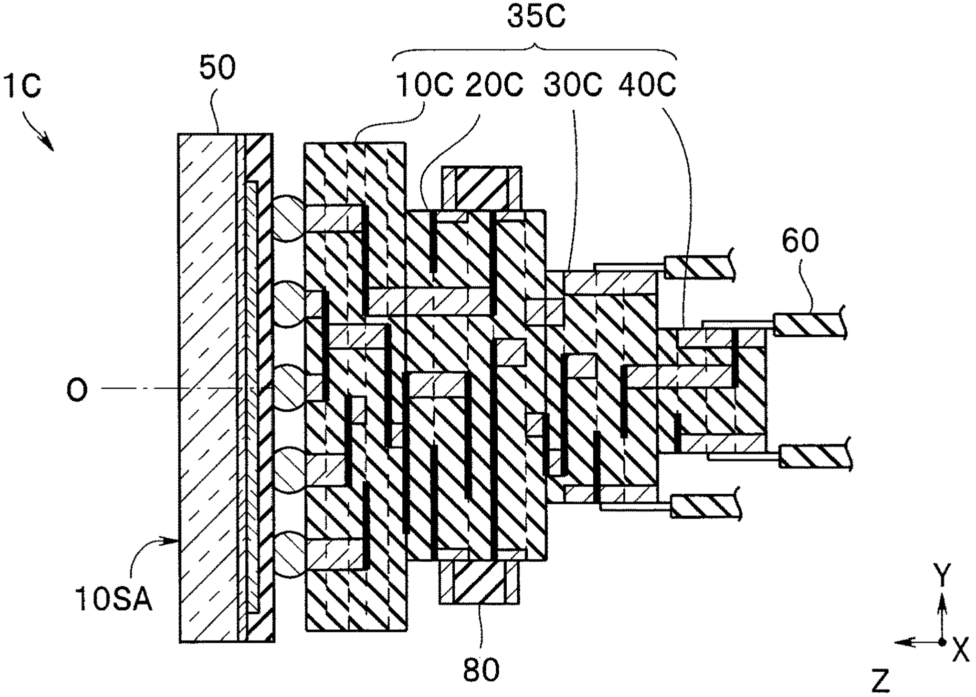
FIG. 13 is a perspective view of wiring plates of the image pickup unit according to Modification 1 of the second embodiment.
Figure 17:
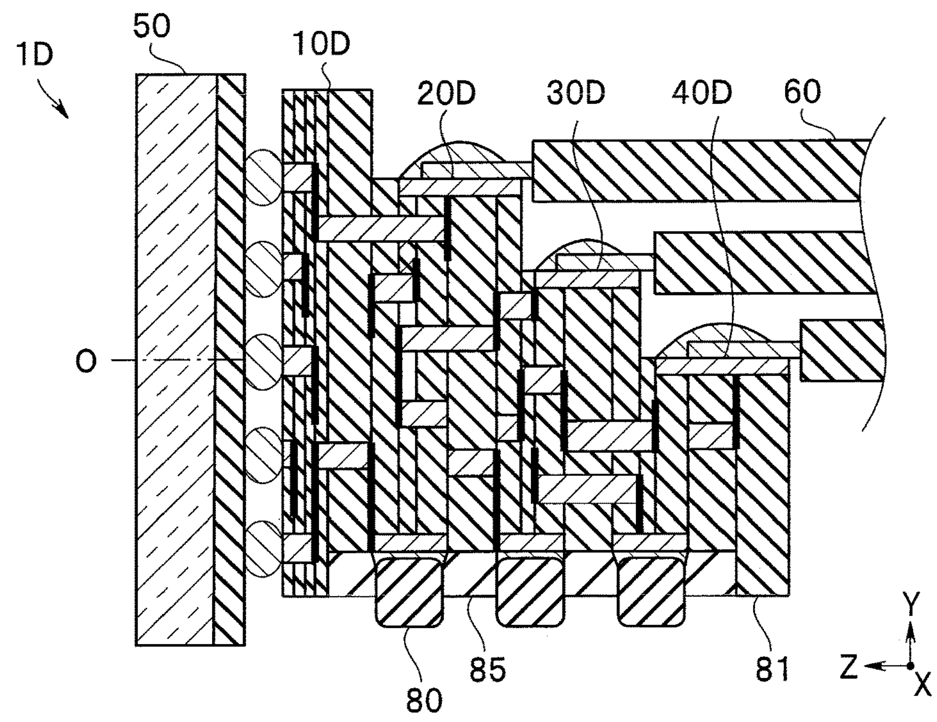
FIG. 17 is a cross-sectional view of the image pickup unit according to Modification 2 of the second embodiment.

In an image pickup unit 1C according to the present modification illustrated in FIGS. 12 and 13, a ceramic solid wiring plate 35C includes a first wiring plate 10C, a second wiring plate 20C, a third wiring plate 30C, and a fourth wiring plate 40C. Note that the image pickup unit 1C is rotationally symmetric by 180° with respect to the optical axis O at the center.

Chip lands 22 that are exposed surfaces of two respective seventh conductor blocks 22C and 22D are provided on the second side surface 20SS1 of the second wiring plate 20C, The chip components 80 such as chip capacitors are mounted extremely near the image pickup device 53. Physical distance between the image pickup device 53 and each chip component 80 is short and a signal transmission pa is unlikely to be affected by parasitic capacitance or the like, and thus the image pickup unit 1C has higher performance than the image pickup unit 1B.

Modification 2 of Second Embodiment

In an image pickup unit 1D according to the present modification illustrated in FIGS. 14 to 17, a solid wiring plate 35D includes a first wiring plate 10D, a second wiring plate 20D, a third wiring plate 30D, and a fourth wiring plate 40D.

The second wiring plate 20D includes the cable lands 28 that are exposed surfaces of conductor blocks on the second side surface 20SS1. The third wiring plate 30D includes the cable lands 38 that are exposed surfaces of conductor blocks on the third side surface 30SS1. The fourth wiring plate 40D includes the cable lands 48 that are exposed surfaces of conductor blocks on the fourth side surface 40SS1.

In the solid wiring plate 35D, a side surface opposite the second side surface 20SS1, a side surface opposite the third side surface 30SS1, and a side surface opposite the fourth side surface 40SS1 constitute a side surface 35SS2. An outer periphery of the side surface 35SS2 forms a bank 81 in a frame shape. A recess C35 is formed in a side surface 10SS2 of the first wiring plate 10D.

As described later, the recess C35 is a recess to be filled with underfill resin 85. The bank 81 prevents the underfill resin 85 from spreading outside.

Figure 18:
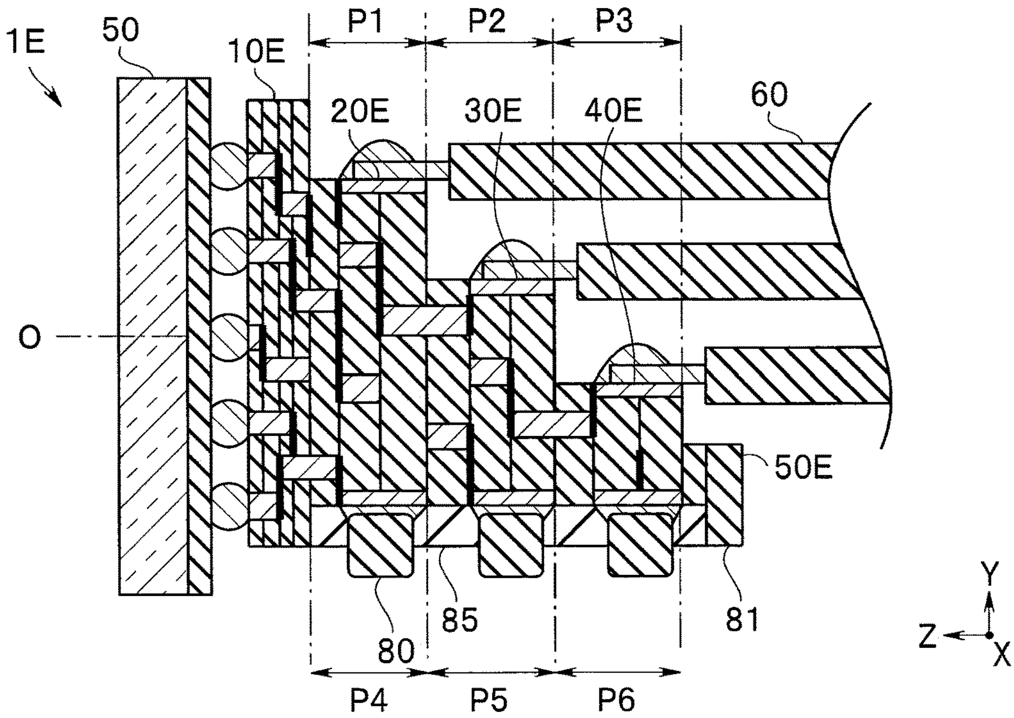
FIG. 18 is a cross-sectional view of an image pickup unit according to Modification 3 of the second embodiment.

The solid wiring plate 35D includes the chip lands 22, 32, and 42 that are exposed surfaces of conductor blocks on the side surface 35SS2. As illustrated in FIG. 18, in the solid wiring plate 35D, the two electrodes of each chip component 80, which are disposed at respective end parts in a long axis direction, are arranged in a direction (X direction) orthogonal to the optical axis O. Thus, the chip components 80 having a large size with a long distance between the two electrodes can be mounted on the solid wiring plate 35D irrespective of the thickness of each sheet constituting the wiring plate.

To improve reliability of bonding of each chip component 80 to the chip lands 22, 32, or 42, the underfill resin 85 is injected into the hank 81 by utilizing the recess C35 after the chip component 80 is mounted. The underfill resin 85 is insulating resin such as epoxy resin, acrylic resin, polyimide resin, silicone resin, or polyvinyl resin.

The solid wiring plate 35D, in which a plurality of wiring plates are stacked and integrated, is more inexpensive, more space-saving, and more reliable than a configuration in which a plurality of wiring plates are bonded by ball soldering. In the solid wiring plate 35D, since side surfaces at which the cable lands 28, 38, and 48 bonded to the cables 60 are disposed on opposite side surfaces at which the chip lands 22, 32, and 42 bonded to the chip components 80 are disposed, the number of assembly processes can be reduced. Moreover, the solid wiring plate 35D has high reliability of bonding of the chip components 80 due to the underfill resin 85 and includes the bank 81 for preventing extrusion at filling with the underfill resin 85. Furthermore, since the long axis direction of each chip component 80 when disposed is orthogonal to the optical axis O, a large-sized chip component can be mounted on the solid wiring plate 35D.

Modification 3 of Second Embodiment

An image pickup unit 1E according to the present embodiment illustrated in FIG. 18 is similar to the image pickup unit 1D. A solid wiring plate 35E of the image pickup unit 1E includes a first a plate 10E, a second wiring plate 20E, a third wiring plate 30E, a fourth wiring plate 40E, and a fifth wiring plate 50E.

The fifth wiring plate 50E at a rear end of the solid wiring plate 35E is a step for facilitating bonding to a cable 60.

In the solid wiring plate 35E, sheets for providing cable lands are same as sheets for providing chip lands, and thus the number of stacked sheets is small, which allows inexpensive manufacturing.

In the solid wiring plate 35E, pitches P1, P2, and P3 between cable lands at a plurality of steps are equal to pitches P4, P5, and P6 between chip lands.

Third Embodiment

Figure 19:
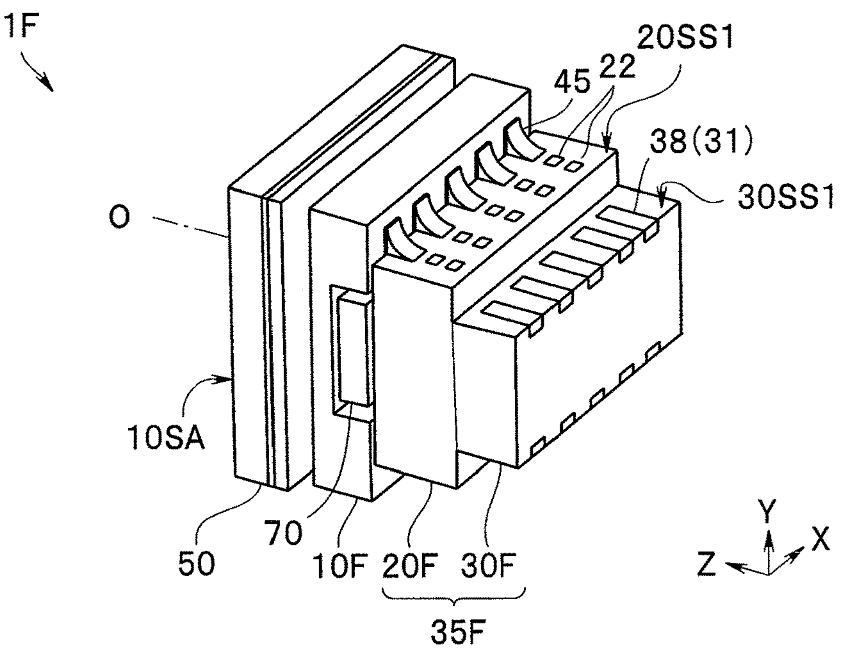
FIG. 19 is a perspective view of wiring plates of an image pickup unit according to a third embodiment.
Figure 20:
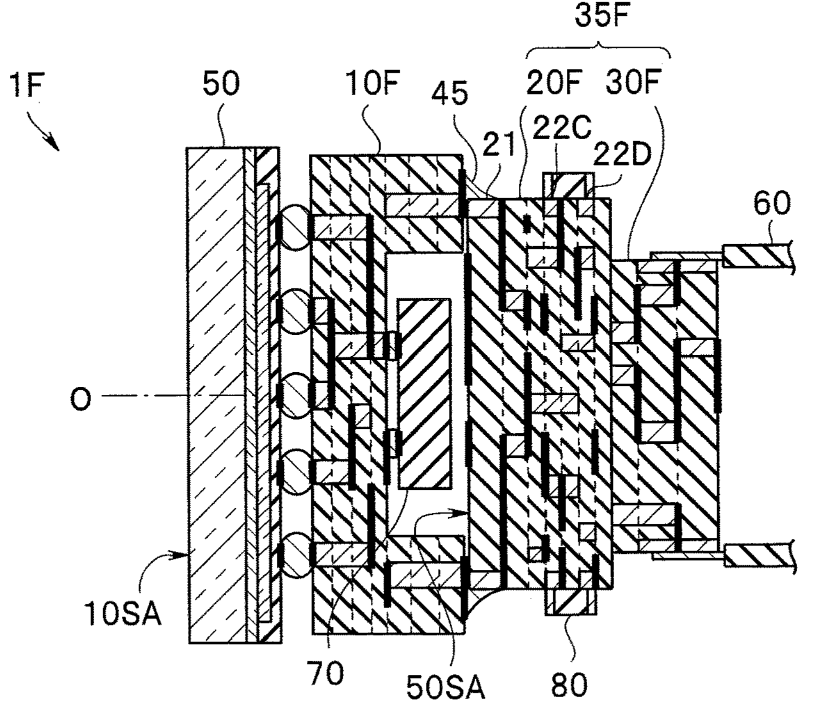
FIG. 20 is a cross-sectional view of the image pickup unit according to the third embodiment.
Figure 20:
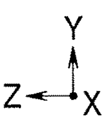

In an image pickup unit 1F according to the present embodiment illustrated in FIGS. 19 and 20, a solid wiring plate 35F includes a second wiring plate 20F and a third wiring plate 30F. The image pickup unit 1F is rotationally symmetric by 180° with respect to the optical axis O at the center.

The second wiring plate 20F includes the fifth electrodes 59 that are exposed surfaces of the first conductor blocks 21 on the fifth principal surface 50SA. The second wiring plate 20F also includes the sixth electrodes 69 that are exposed surfaces of the first conductor blocks 21 and the two chip lands 22 that are exposed surfaces of the two seventh conductor blocks 22C and 22D on the second side surface 20SS1.

The fourth electrodes 49 of a first wiring plate 10F are bonded to the fifth electrodes 59 and the sixth electrodes 69 by the solder 45. A chip component 80 is bonded to each pair of two chip lands 22.

The image pickup unit 1F has high strength of bonding between the first wiring plate 10F and the second wiring plate 20F and is excellent in reliability. Moreover, since the chip components 80 are mounted near the image pickup device 53, the image pickup unit 1F has high performance.

<Endoscope>

Figure 21:
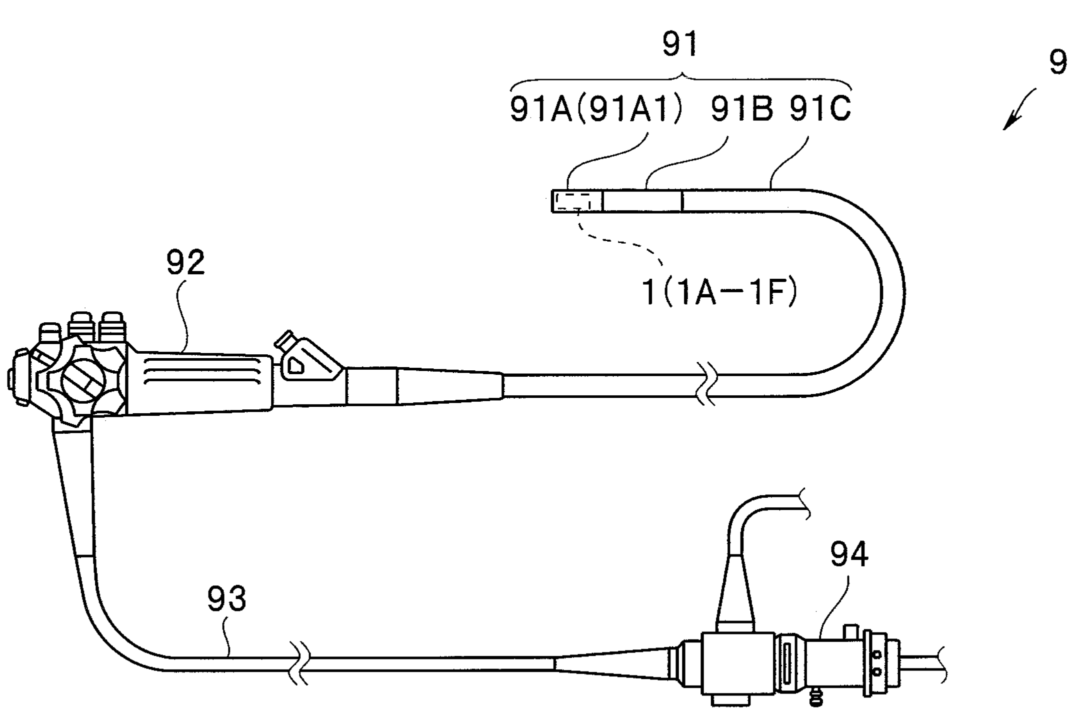
FIG. 21 is a perspective view of an endoscope according to each embodiment.

An endoscope 9 according to the present embodiment illustrated in FIG. 21 includes an insertion portion 91, an operation portion 92, a universal code 93, and a connector 94.

The insertion portion 91 having an elongated pipe shape is inserted into a body cavity of a living body. The insertion portion 91 includes a distal end portion 91A, a bending portion 91B, and a flexible tube 91C continuously provided in order from a distal end side and has flexibility as a whole. The distal end portion 91A includes a rigid member 91A1 in which the image pickup unit 1 is disposed. The bending portion 91B bends in up, down, right, and left directions in accordance with a rotational operation of a bending knob of the operation portion 92 for performing a bending operation.

The flexible tube 91C is a flexible tubal member that is passively bendable. For example, a treatment instrument insertion channel, a signal line, and a fiber bundle are inserted inside the flexible tube 91C. The signal line extends from the image pickup unit built in the distal end portion 91A to the universal code 93 through the operation portion 92. The fiber bundle guides light from a light source device as an external instrument to a distal end surface of the distal end portion 91A.

The operation portion 92 is continuously provided at a proximal end portion of the insertion portion 91 and includes a plurality of operation members and the like. The universal code 93 extends from the operation portion 92. The connector 94 is a connection member for connecting the universal code 93 to an external instrument.

The endoscope 9 includes the image pickup unit 1 disposed in the rigid member 91A1. As described above, the image pickup unit 1 has high reliability, and thus the endoscope 9 has high reliability.

Needless to say, the endoscope 9, which includes any of the image pickup units 1A to 1F, has same effects as the image pickup units 1A to 1F.

The endoscope may be a flexible endoscope including a flexible insertion portion or may be a rigid endoscope including a rigid insertion portion. The endoscope may be used in medical and industrial fields, Each wiring plate is a ceramic wiring plate in above-described examples but may be a glass epoxy wiring plate.

The present invention is not limited to the above-described embodiments and the like but may be provided with various kinds of modification, combination, and application without departing from the scope of the invention.

What is claimed is:

1. An image pickup unit comprising:

an image pickup substrate having a first principal surface and a second principal surface and including an image pickup device, a first electrode of the image pickup device being connected to a second electrode disposed on the second principal surface;

a first wiring plate having a third principal surface, a fourth principal surface, and a first side surface, a third electrode on the third principal surface being bonded to the second electrode;

a second wiring plate having a fifth principal surface, a sixth principal surface, and a second side surface, a fifth electrode on the fifth principal surface and a sixth electrode on the second side surface being bonded to a fourth electrode on the fourth principal surface of the first wiring plate by using solder, the sixth electrode being extended from the fifth electrode, a third wiring plate having a seventh principal surface and a third side surface, the seventh principal surface contacting the sixth principal surface; and a cable bonded to a cable land on the third side surface, wherein a first conductor block is embedded in the second wiring plate, an exposed surface of the first conductor block on the fifth principal surface being the fifth electrode, an exposed surface of the first conductor block on the second side surface being the sixth electrode, the solder bonding the fourth electrode and the sixth electrode forms a fillet;

the second wiring plate and the third wiring plate are an integrated solid ceramic wiring plate; and a second conductor block is embedded in the third wiring plate, an exposed surface of the second conductor block on the third side surface being the cable land.

2. The image pickup unit according to claim 1, wherein the solder bonds the fourth electrode and the fifth electrode.

3. The image pickup unit according to claim 1, wherein the fourth electrode is extended to a region not facing the fifth principal surface of the second wiring plate.

4. The image pickup unit according to claim 1, wherein the second wiring plate includes a groove in a fifth side surface orthogonal to the first side surface, the groove having a conductor film as a wall surface, the first wiring plate includes an eighth electrode on the fourth principal surface, and solder filling the groove of the second wiring plate bonds the conductor film and the eighth electrode.

5. An image pickup unit comprising:

an image pickup substrate having a first principal surface and a second principal surface and including an image pickup device, a first electrode of the image pickup device being connected to a second electrode disposed on the second principal surface;

a first wiring plate having a third principal surface, a fourth principal surface, and a first side surface, a third electrode on the third principal surface being bonded to the second electrode; and a second wiring plate having a fifth principal surface, a sixth principal surface, and a second side surface, a fifth electrode on the fifth principal surface and a sixth electrode on the second side surface being bonded to a fourth electrode on the fourth principal surface of the first wiring plate by using solder, the sixth electrode being extended from the fifth electrode, wherein a first conductor block is embedded in the second wiring plate, an exposed surface of the first conductor block on the fifth principal surface being the fifth electrode, an exposed surface of the first conductor block on the second side surface being the sixth electrode, the solder bonding the fourth electrode and the sixth electrode forms a fillet;

the second wiring plate is a multi-layer board in which a plurality of wiring layers are stacked in an optical axis direction, the plurality of wiring layers including two wiring layers in each of which a third conductor block and a fourth conductor block are embedded, an interval between the two wiring layers in each of which the fourth conductor blocks are embedded among the plurality of wiring layers is substantially equal to an interval between two chip electrodes of a chip component, the chip electrodes are bonded to chip lands that are exposed surfaces of the fourth conductor blocks of the two wiring layers, the exposed surfaces being exposed on one side surface of the second wiring plate, the cable is bonded to cable lands that are exposed surfaces of the third conductor blocks of the two wiring layers, the exposed surfaces being exposed on a side surface opposite the one side surface, and an interval between the chip lands is equal to an interval between the cable lands in the optical axis direction.

6. An image pickup unit comprising:

an image pickup substrate having a first principal surface and a second principal surface and including an image pickup device, a first electrode of the image pickup device being connected to a second electrode disposed on the second principal surface;

a first wiring plate having a third principal surface, a fourth principal surface, and a first side surface, a third electrode on the third principal surface being bonded to the second electrode;

a second wiring plate having a fifth principal surface, a sixth principal surface, and a second side surface, the second wiring plate being a multi-layer board in which a plurality of wiring layers are stacked in an optical axis direction, an interval between two wiring layers in each of which a third conductor block and a fourth conductor block are embedded among the plurality of wiring layers being substantially equal to an interval between two chip electrodes of a chip component;

the chip component the two chip electrodes of which are bonded to two chip lands that are exposed surfaces of the fourth conductor blocks of the two wiring layers, the exposed surfaces being exposed on the second side surface; and a cable bonded to any of cable lands that are exposed surfaces of the third conductor blocks of the two wiring layers, the exposed surfaces being exposed on a side surface opposite the second side surface, wherein a disposition pitch between the chip lands is equal to a disposition pitch between the cable lands in the optical axis direction.

7. The image pickup unit according to claim 1, wherein the second wiring plate is a multi-layer board in which a plurality of wiring layers are stacked in an optical axis direction, the plurality of wiring layers including two wiring layers in each of which a third conductor block and a fourth conductor block are embedded, an interval between the two wiring layers in each of which the fourth conductor blocks are embedded among the plurality of wiring layers is substantially equal to an interval between two chip electrodes of a chip component, the chip electrodes are bonded to chip lands that are exposed surfaces of the fourth conductor blocks of the two wiring layers, the exposed surfaces being exposed on one side surface of the second wiring plate, the cable is bonded to cable lands that are exposed surfaces of the third conductor blocks of the two wiring layers, the exposed surfaces being exposed on a side surface opposite the one side surface, and an interval between the chip lands is equal to an interval between the cable lands in the optical axis direction.

8. The image pickup unit according to claim 1, wherein the image pickup device comprises an image sensor.

9. An endoscope comprising the image pickup unit according to claim 1.

10. The image pickup unit according to claim 5, wherein the image pickup device comprises an image sensor.

11. An endoscope comprising the image pickup unit according to claim 5.

12. The image pickup unit according to claim 5, further comprising:

a third wiring plate having a seventh principal surface and a third side surface, the seventh principal surface contacting the sixth principal surface; and a cable bonded to a cable land on the third side surface, wherein the second wiring plate and the third wiring plate are an integrated solid ceramic wiring plate.

13. The image pickup unit according to claim 5, wherein the solder bonds the fourth electrode and the fifth electrode.

14. The image pickup unit according to claim 5, wherein the fourth electrode is extended to a region not facing the fifth principal surface of the second wiring plate.

15. The image pickup unit according to claim 12, wherein a second conductor block is embedded in the third wiring plate, an exposed surface of the second conductor block on the third side surface being the cable land.

16. The image pickup unit according to claim 5, wherein the second wiring plate includes a groove in a fifth side surface orthogonal to the first side surface, the groove having a conductor film as a wall surface, the first wiring plate includes an eighth electrode on the fourth principal surface, and solder filling the groove of the second wiring plate bonds the conductor film and the eighth electrode.

* * * * *